United States Patent [19]

McGauley et al.

[11] Patent Number: 5,899,998
[45] Date of Patent: May 4, 1999

[54] METHOD AND SYSTEM FOR MAINTAINING AND UPDATING COMPUTERIZED MEDICAL RECORDS

[75] Inventors: James L. McGauley, Ann Arbor, Mich.; Christopher Krumme, Aurora, Ill.

[73] Assignee: Medcard Systems, Inc., Ann Arbor, Mich.

[21] Appl. No.: 08/521,826

[22] Filed: Aug. 31, 1995

[51] Int. Cl.⁶ .................................................. G06F 17/30
[52] U.S. Cl. ................................ 707/104; 707/8; 707/10; 705/3
[58] Field of Search .................................... 370/477, 235; 395/76, 800, 608, 768, 615, 203, 601, 200.18, 200.09, 202, 769, 238; 340/825.54; 379/221; 707/8, 10, 202, 104; 705/40, 3; 382/380; 445/466

[56] References Cited

U.S. PATENT DOCUMENTS

| | | | |
|---|---|---|---|
| 4,429,372 | 1/1984 | Berry et al. | 395/769 |
| 4,491,725 | 1/1985 | Pritchard | 705/2 |
| 4,812,628 | 3/1989 | Boston et al. | 395/238 |
| 4,816,653 | 3/1989 | Anderl et al. | 235/380 |
| 4,821,175 | 4/1989 | Hikita et al. | 395/608 |
| 4,858,121 | 8/1989 | Barber et al. | 395/202 |
| 4,868,866 | 9/1989 | Williams, Jr. | 340/825.31 |
| 4,970,658 | 11/1990 | Durbin et al. | 395/76 |
| 5,021,949 | 6/1991 | Morten et al. | 395/200.09 |
| 5,149,945 | 9/1992 | Johnson et al. | 235/380 |
| 5,212,789 | 5/1993 | Rago | 707/8 |
| 5,230,073 | 7/1993 | Gausmann et al. | 395/603 |
| 5,230,075 | 7/1993 | Premerlani et al. | 395/601 |
| 5,291,399 | 3/1994 | Chaco | 705/3 |
| 5,295,064 | 3/1994 | Malec et al. | 395/201 |
| 5,299,259 | 3/1994 | Otto | 379/221 |
| 5,327,426 | 7/1994 | Dolin, Jr. et al. | 370/235 |
| 5,361,202 | 11/1994 | Doue | 705/3 |
| 5,506,984 | 4/1996 | Miller | 707/10 |
| 5,530,855 | 6/1996 | Satoh et al. | 395/617 |
| 5,541,583 | 7/1996 | Mandelbaum | 340/825.54 |
| 5,546,580 | 8/1996 | Seliger et al. | 707/8 |
| 5,560,005 | 9/1996 | Hoover et al. | 707/10 |
| 5,568,489 | 10/1996 | Yien et al. | 370/477 |
| 5,574,904 | 11/1996 | Yunoki et al. | 395/601 |
| 5,583,914 | 12/1996 | Chang et al. | 445/466 |
| 5,603,026 | 2/1997 | Demers et al. | 395/608 |
| 5,613,012 | 3/1997 | Hoffman et al. | 382/380 |
| 5,625,818 | 4/1997 | Zarmer et al. | 395/615 |
| 5,627,972 | 5/1997 | Shear | 395/200.18 |
| 5,630,159 | 5/1997 | Zancho | 395/800 |
| 5,640,561 | 6/1997 | Satoh et al. | 707/202 |
| 5,644,727 | 7/1997 | Atkins | 705/40 |
| 5,659,741 | 8/1997 | Eberhardt | 707/104 |

OTHER PUBLICATIONS

Yeo et al. "Submission of Transactions from Mobile Workstations in a Cooperative Multidatabase Environment", Distributed Computing Systems, 1994 Int'l Conf., pp. 372–379.

Huang et al. "Object Allocation in Distributed Databases and Mobile Computers", Data Engineering, 1994 10th Int'l Conf., pp. 20–29.

Ciciani et al. "Analysis of Concurrency–Coherency Control Protocols for Distributed Transaction Processing Systems with Regional Locality ", IEEE Transacitons on Software Engineering, v18, n10, pp. 899–914, Oct. 1992.

*Primary Examiner*—Wayne Amsbury
*Assistant Examiner*—Charles L. Rones
*Attorney, Agent, or Firm*—Harness, Dickey & Pierce, P.L.C.

[57] ABSTRACT

A distributed database architecture stores medical information in a self-updating system that employs point-of-service stations disposed at convenient medical service locations. Each patient carries a portable data carrier such as a smart card that contains the patient's complete medical history. Interaction between the portable data carriers and the point-of-service stations effects a virtual communication link that ties the distributed databases together without the need for online or live data connections. The point-of-service stations are also interconnected over a communications network through a switching station that likewise does not rely on online, live communication. The database system uses an object-oriented update object to distribute data that has been generated when a portable data carrier is not physically present and to automatically distribute data without the necessity of accessing a masterfile.

76 Claims, 12 Drawing Sheets

200 — FIELD OBJECT

| Field Type Identifier | Field Length | Field Value |
|---|---|---|

210 — COLLECTION OF FIELD OBJECTS

| Field Type Identifier | Field Length | Field Value |
|---|---|---|
|  |  |  |
|  |  |  |
|  |  |  |
|  |  |  |

FIG. 2

220 — RECORD OBJECT

| Record Type Identifier | Unique Record Object Identifier | Collection Of Field Objects |
|---|---|---|

230 — COLLECTION OF RECORD OBJECTS

| Record Type Identifier | Unique Record Object Identifier | Collection Of Field Objects | | |
|---|---|---|---|---|
| | | Field Type | Field Length | Field Value |
| | | | | |
| | | | | |
| | | | | |

FIG. 3

140 — SWITCHING STATION

Receive Update Objects From POS Stations & From Administrative Services System

Route Update Objects To Designated POS Stations

Route Update Objects To Administrative Services System

Store Update Objects Until Acknowledgements Are Received

Send Update Objects To POS Stations And To Administrative Services System

FIG. 8

128 —— COMMUNICATION MANAGER

1. Receive Update Object From Switching Station

2. Send Update Object To Patient Manager

123 —— PATIENT MANAGER

Apply Update Objects To This Station's Database

3. Sort Update Objects By Patient Identification

4. Send Update Object To Database Manager Based On Patient Identification

6. Sort Update Objects By Type (Add, Delete, Replace)

7. Send "Add Record Object" to Database Manager

9. Send "Delete Record Object" To Database Manager

11. Send "Replace Record Object" To The Database Manager

116 —— DATABASE MANAGER

5. Add Update Objects To Collection Of Updates In This Station's Database Based On Patient Identification 8. Add Record Object To This Station's Database 10. Delete Record Object From This Station's Database 12. Replace Record Object In This Station's Database

122 —— DATABASE

FIG. 11

METHOD AND SYSTEM FOR MAINTAINING AND UPDATING COMPUTERIZED MEDICAL RECORDS

BACKGROUND AND SUMMARY OF THE INVENTION

A. Field of the Invention

The present invention relates generally to computerized medical information systems. More specifically, it relates to maintaining and updating computerized medical records.

The invention is based on a distributed database network architecture, in which a plurality of portable data carriers (PDCs) and point-of-service (POS) stations interact to maintain the currency of the medical records of a plurality of patients. Each PDC contains the medical record of an individual patient. Each POS station contains a system for generating and propagating medical data specific to that medical care site.

The PDCs and POS stations contain independent, but interrelated, databases; and a major function of the presently described invention is to keep the information in these databases current.

In addition to serving as one of the database repositories in this network, each PDC also serves as a communication link between the POS stations. Each patient carries their own medical record from one station to another on their own PDC.

Furthermore, the invention utilizes object-oriented tools and structures that include: (1) dynamic objects called "update objects" and (2) data processing "rule sets" which are stored throughout the above described network, working together, these update objects and rule sets establish, route, organize, store and update the medical information of a plurality of patients.

B. Description of Related Art

The healthcare industry has long recognized the need for a computerized medical information system that can maintain a comprehensive and current record of each patient's medical status over space and time.

Although keeping such information in computerized databases might seem simple, providing efficient and cost-effective access to those databases and keeping all data in the databases current, are daunting tasks due to some technical inefficiencies in traditional distributed database systems, and due to the size and mobility of patient populations.

Whereas, it has been possible to successfully implement traditional centralized on-line computer information systems for geographically limited populations, such as within hospitals, it has not been possible to simply scale-up these systems to accommodate larger, more disperse patient populations in the outpatient setting.

The complex, wide-spread interactions of medical outpatient care require a wide area network architecture. However, available distributed database networks exhibit significant shortcomings when they are applied to electronic data interchange applications that entail complex independent transactions at numerous disparate point-of-service locations.

The major problems that make traditional network models unsuitable for many point-of-service applications, such as outpatient medical care, are: (1) inefficient access to needed data, (2) difficulty in maintaining data currency throughout the system and (3) cost.

From the data access standpoint, traditional transaction-oriented networks define a master data file which must be coordinated and updated at one main site and then must be made available, in whole or in part, to peripheral dependent locations.

In order to have access to current data, these traditional systems must be continuously available on-line; and as the complexity of the transaction-based application increases, overload and bottleneck problems ensue; and the communication channels become more complicated and costly. Furthermore, the integrity of the whole network continuously and precariously depends on the reliability of these physical communication channels.

To date, accessing a central file, at some point, is the only networking solution that allows for the coordination of data updates that have been generated at geographically distinct locations. And unfortunately, all of these network systems experience overload, bottleneck, service interruption or coordination delay problems, because of their need to update and then redistribute, data from a masterfile.

Outpatient medical transactions are so diverse, as well as being so geographically and temporally complex, that the anticipated problems of data access, data currency and cost of the traditional centralized systems, become prohibitive. These are the primary reasons that, currently, there are no successful, broad-based computerized outpatient medical record systems.

SUMMARY OF THE INVENTION

The present invention takes a different approach. It does not depend on the presence of a central database, or a single masterfile. It is a new type of distributed database network system in which medical data items are automatically propagated from their sites of origin to several different memory storage sites, independently and selectively. The memory sites exist in: (1) portable data carriers (PDC), (2) medical point-of-service (POS) stations and (3) administrative services systems.

Although the presently described system is applicable to inpatient medical care, it is most advantageous in the outpatient setting.

In the presently preferred embodiment, the PDC is a microprocessor integrated circuit chip card, commonly known as a smart card. This card serves as a data storage device on which patients carry a copy of their own medical record.

Each card can carry a significant amount of medical data. In the present embodiment, this includes, but is not restricted to: diagnoses, surgeries, obstetrical data, status of therapeutic treatments, diagnostic test results, current and past medications, allergies, diet, durable medical equipment, blood type, advanced directives, immunizations, birth data, social history, family history, physician office visits, hospitalizations and emergency room visits. In addition, the card carries physician orders, such as medication prescriptions, laboratory or X-ray tests, referrals to consultant physicians, surgical procedures and the like. All of this data is directly transported between the POS stations of the system on the PDCs.

The POS stations are computer systems positioned at locations where patients receive medical care, such as physician offices, pharmacies, laboratories, radiology units, hospitals, diagnostic and treatment centers, emergency treatment sites and urgent care centers. Each of the POS stations may be custom-configured to that provider's specific medical application.

For example, a physician office POS station may, among other functions, generate new diagnoses and physician orders; and may store and have access to the entire medical record of all the patients that are cared for at that particular site. Whereas, a pharmacy POS station, in addition to other functions, may read the medication prescription orders that are designated on the patient's PDC; and further, may indicate on the PDC that the medication has been dispensed. However, the pharmacy POS station may not have read or write access to any other portion of the patient's PDC record.

This independent PDC-POS database design allows "patient specific" and "site specific" medical data to be present when and where it is needed, at every medical POS location. Each patient carries their own medical record with them to each POS site, thus resolving the issue of timely and efficient access to data. Bottleneck, system overload and service interruption problems are avoided.

Besides serving as data memory sites, the PDCs also serve as one of the main communication links between POS stations. Stored within their PDC, patients actually carry their medical data from one POS station to another. We are describing this aspect of the invention as "off-line" communication, to distinguish it from "traditional on-line" communication. For transaction-based applications, "on-line" implies continuous availability of a physical telecommunication link and live or real-time data transfer. In contrast, by carrying their own data with them, the PDCs allow intermittent, focused, "off-line" coupling, which is much more efficient and much less expensive.

By way of brief illustration, when a patient visits their doctor, the patient's PDC is read by the doctor's POS station and this automatically transfers medical information between the PDC and the station, so that the more current data is propagated and stored in both places.

Thereafter, the doctor may diagnose an illness, and prescribe certain medications. This information is input and stored in the doctor's POS station and also transferred to the patient's PDC before they leave the office.

Later, when the patient visits the pharmacy to fill the prescription, the patient's PDC is read by the POS station at the pharmacy. This causes the current prescription information to be propagated to the pharmacy station. It may not be necessary for the pharmacy POS station to have access to all of the medical information on the PDC. Indeed, some of the information may be confidential or unnecessary to filling the prescription. The internally stored rule sets in the pharmacy POS station govern what information can be obtained from the PDC and what information is excluded.

The pharmacy then inputs its data related to filling the prescription, thus updating the PDC further. The pharmacy POS station also stores the data it generated in its own internal memory.

In the preceding illustration, only two stations were described. However, as indicated previously, the system contemplates a plurality of POS stations, each being custom-configured to that provider's medical application.

These POS stations are all in "virtual" communication with each other because the collective rule sets of the system are designed to propagate data from one station to another, using the PDCs as the communication medium rather than traditional telecommunication channels.

Furthermore, a second type of "virtual" communication system has been designed which does utilize traditional telecommunication channels; but describes an alternate method of propagating data over these channels. The data is transmitted via "update objects."

The core of each update object is an element of information or an item of data that has been generated by a medical transaction at a POS station. Examples of such data would be an X-ray report or a laboratory test result. In addition to this basic core of medical data, each update object also contains processing tags. These tags, along with corresponding data processing "rule sets" located throughout the system, guide each update object to its targeted PDC, POS and administrative databases, independently. Furthermore, the processing tags and rule sets also function to automatically assimilate the data element into the independent databases.

The update object is designed to distribute data that has been generated when a PDC is not physically present, such as a laboratory test result which becomes available after the patient has already left the laboratory. Also, it is designed to automatically distribute data without needing to access a masterfile.

For example, an update object may be created at a laboratory POS station. The update object contains a test result and is tagged with specific destination identifiers such as the POS address of the patient's primary physician.

The update object is then routed through a switching station which is essentially an electronic data exchange system containing rule sets designed to propagate the medical data over traditional communication channels from one network POS station to any other station. The system is not dependent on a specific method of data transmission.

This system does differ from traditional switching mechanisms, in that, rather than routing update information to a single masterfile, each data element is automatically routed to any of a number of distributed databases throughout the network. Furthermore, all data is routed selectively, meaning that it is only transported to locations at which it is needed. This system provides significant data processing efficiency. Also, communication between each POS station and the switching station only needs to occur intermittently, resulting in significant cost savings.

When the update object arrives at the physician's POS station, it is stored in the database and it is also transferred to the patient's PDC, the next time the patient arrives for medical care. In addition to direct PDC-POS communication linkages, this update object-switching station design provides a second automatic and selective mechanism for the POS stations and the PDCs to remain current without needing to access a masterfile.

In addition to the above advantages, each update object persists in critical locations throughout the network, until the data element it contains has successfully reached all designated databases. This feature provides significant data security and does not rely on the continuous integrity of the telecommunication linkages to assure that data is appropriately propagated.

As mentioned previously, this system also contains an administrative services system which provides the management services related to medical activities services such as data backup, billing, medical and financial auditing, and report generation.

One of the key concepts of this invention is the establishment of a network of truly independent databases, which are connected by "virtual" communication systems and are automatically modified and kept current, without accessing a masterfile. This concept is made functional by combining PDCs, which are both independent databases and "off-line" communication channels, with independent POS stations and administrative services systems, all utilizing flexible and unique computer tools and rules.

This invention provides a practical, efficient, and cost-effective solution to the problems associated with complex, high-volume, transaction-oriented networking applications, such as outpatient medical information systems.

BRIEF DESCRIPTION OF THE DRAWINGS

FIG. 2 is a block diagram illustrating the presently preferred field object data structure;

FIG. 3 is a block diagram illustrating the presently preferred record object data structure;

FIG. 8 is a block diagram of the switching station architecture;

FIG. 11 is a block diagram illustrating the process by which an update object received from a switching station is propagated;

DESCRIPTION OF THE PREFERRED EMBODIMENT

II System Overview

Figure 1:
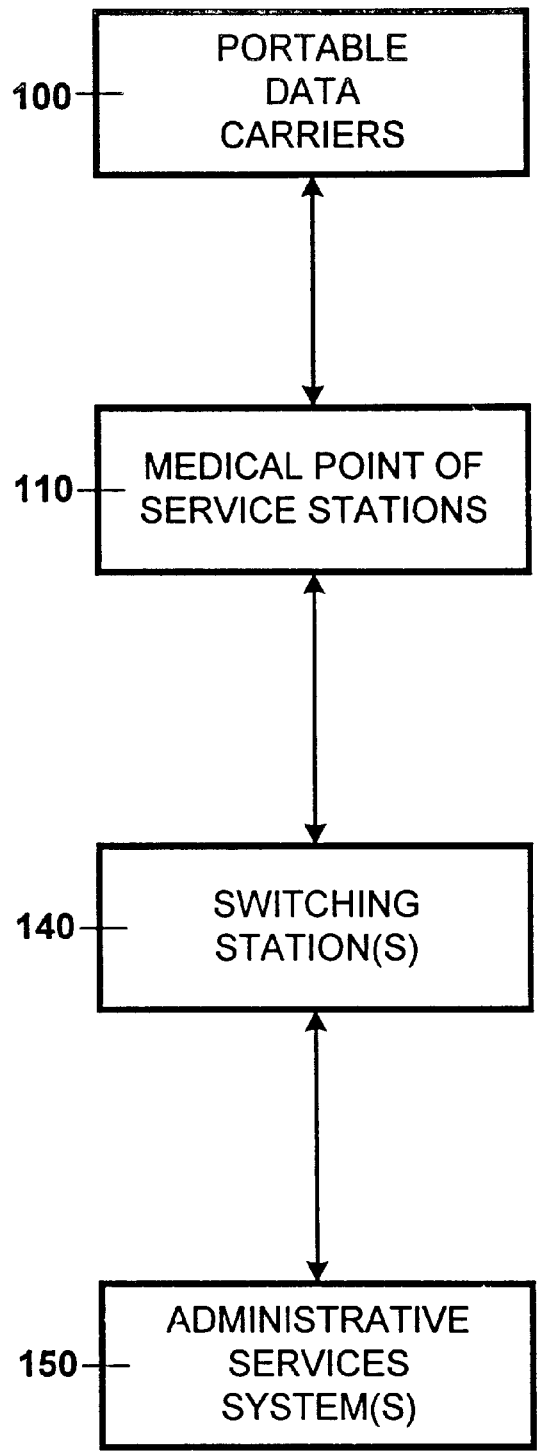
FIG. 1 is a system overview block diagram of the presently preferred system for maintaining and updating computerized medical records.

FIG. 1 illustrates the basic components of the presently preferred medical information system. The system includes a plurality of portable data carriers (PDCs) 100, and medical point-of-service (POS) stations 110, one or more switching stations 140 and one or more administrative services systems 150.

A Portable Data Carrier 100

The presently preferred PDC is an integrated electronic circuit chip card containing a microprocessor and memory and it is commonly known as a "smart card." It has data processing and memory capabilities. It may contain an independent, on-board power source and a digital display. It serves as a data storage medium and a communication device.

The smart card is presently preferred, because it is relatively economical and may easily be carried in the purse or wallet. It has sufficient memory capacity to store a patient's entire medical record; it has processing capabilities to handle changes in the medical record; it can accommodate administrative functions such as demographic changes and financial transactions; and it has numerous inherent security features to accommodate medical privacy and confidentiality concerns.

By integrating software and hardware design, each PDC is structured to communicate with a plurality of medical POS stations. In the presently preferred embodiment, the PDC communicates with the POS stations through electric contacts, although contactless interface is also possible.

Figure 6:
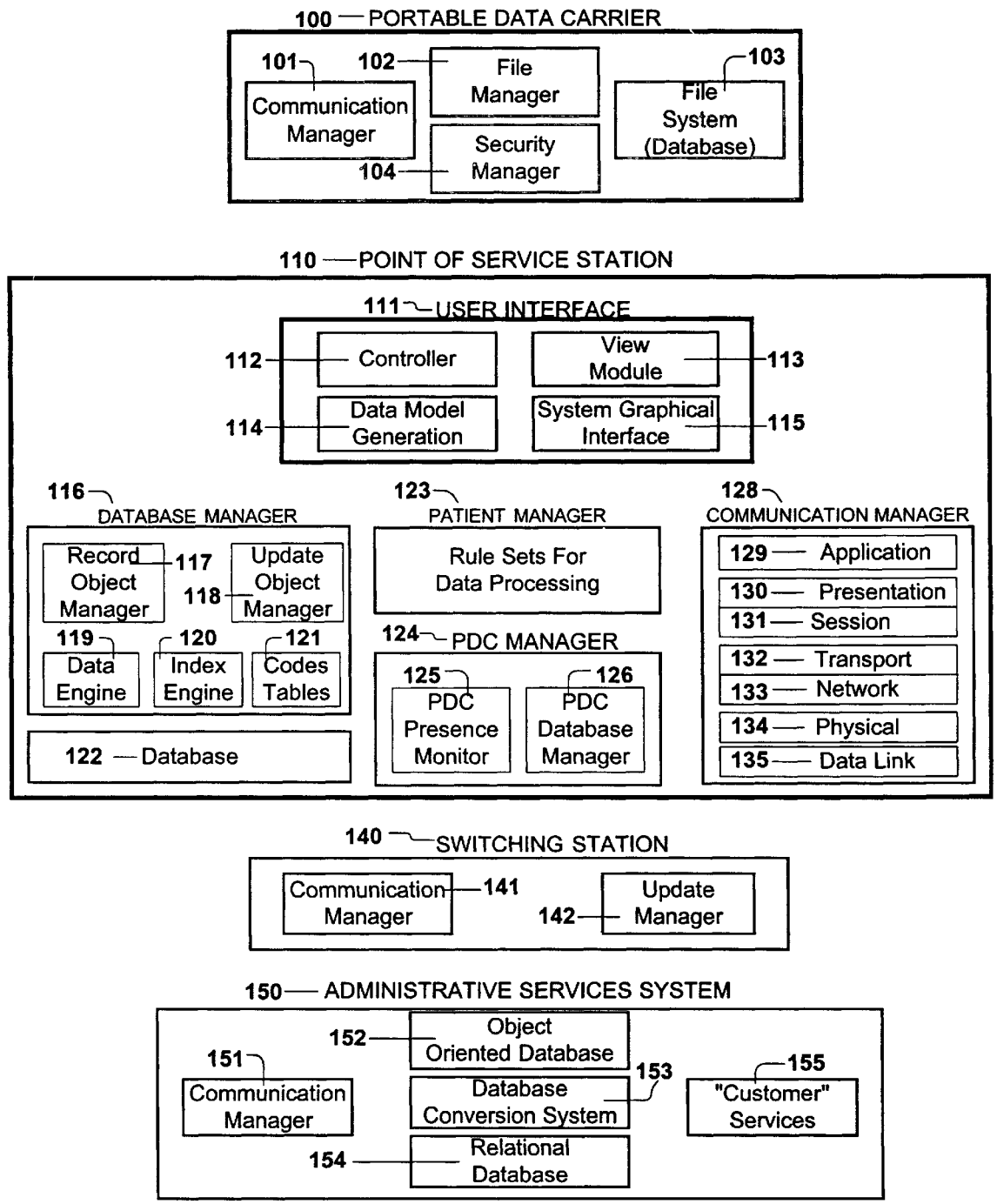
FIG. 6 is a block diagram illustrating the principal subsystems employed in the portable data carrier, the point-of-service station, the switching station and the administrative services system.

As depicted in FIG. 6, the presently utilized PDC conceptually has four principle subsystems: a communication manager 101, a file manager 102, a security manager 104 and a file system (database) 103. These will be described later.

B Point-of-Service Station 110

A medical POS station contains the computer system located at any site where medical services can be provided. These sites include, but are not restricted to, physician offices, diagnostic and therapeutic treatment centers, laboratories, radiology departments, emergency and urgent care treatment sites, pharmacies, hospitals and durable medical equipment suppliers.

In the presently preferred embodiment, the hardware and software at each site are specific for the particular type of medical service provided there. A POS station may be implemented using a variety of different personal computers loaded with the system's specific operating programs described herein. Various peripheral devices such as touchscreens, scanners and devices with digital interfaces such as laboratory test equipment may also be utilized.

The presently preferred embodiment uses a true multitasking operating system, IBM's OS/2. This allows a POS operator to interact with the system with no perceived delay while the PDC is concurrently being interrogated and updated. It also allows several different application programs to run simultaneously. This could be advantageous in medical offices that want to use their POS stations for functions such as word processing, or out-of-system billing or record keeping.

The present system utilizes an object-oriented language, C++ and object-oriented program and system designs.

Referring to FIG. 6, presently, the major POS station subsystems are: user interface 111, database manager 116, database 122, patient manager 123, PDC manager 124 and communication manager 128. These will be described in more detail later.

C Switching Station 140

The presently preferred embodiment uses asynchronous modems to connect each POS station to a switching station. Communications over these modems are encrypted to help protect the security of the system and to preserve the confidentiality of individual patient's medical information.

The present design utilizes intermittent communication of batched data. The data that is generated at each POS station is temporarily stored on site and then transmitted to a switching station, using an "end-of-day" or an "as-needed" routine. This is more efficient, less expensive and more reliable than continuous on-line communication.

Each switching station may be configured with various combinations of PCs, minicomputers, or mainframes. In the presently preferred embodiment, the switching station is a network of PCs. Each PC contains: a communication manager module 141 and an "update manager" module 142 (FIG. 6). Together, these two units organize and direct the routing of data between various POS stations and also between each POS station and the administrative services system.

D Administrative Services System 150

An administrative services system deals with the management issues related to medical care. The types of services provided are optional and can include functions such as data backup, billing, auditing, data analysis and reporting. Each system can be constructed using various hardware and software combinations to provide particular "customer services." "Customer" refers to anyone who utilizes or benefits from the services of the system, such as patients, care providers, healthcare managers, healthcare payers and researchers.

Each administrative services system may be configured utilizing various combinations of PC's, minicomputers or mainframes. The presently preferred embodiment builds the system around a microcomputer or minicomputer which contains: a communication manager 151, an object-oriented database 152, a database conversion system 153, a relational database 154 and an array of "customer services" 155. See FIG. 6.

Over secure channels, the communication manager coordinates bi-directional communication with the switching station. It also provides "external" connections with the information systems of customers such as healthcare managers, payers and researchers.

The object-oriented database maintains a copy of the medical record of all patients using this system. It maintains records in the same format as the PDC and POS databases; and can be used as a backup resource if there is a breakdown in the PDC-POS-switching station portion of the system.

This preferred embodiment further contains a database conversion system which converts the object-oriented database to a relational database. Incorporating a common-format, standardized database structure and language into the present invention, facilitates functions such as report generation and communication with external commercial systems such as those commonly used by healthcare managers, payers and researchers.

The relational database can be used to simplify numerous administrative functions such as financial transactions (including billing, payment and account settlements), auditing, quality assurance, risk management and statistical analysis reporting.

III Data and Database Structures

See FIGS. 2, 3, 4, 5, and 6.

A Overview

The presently preferred embodiment of this invention utilizes object-oriented programming. C++ language is used.

Figure 4:
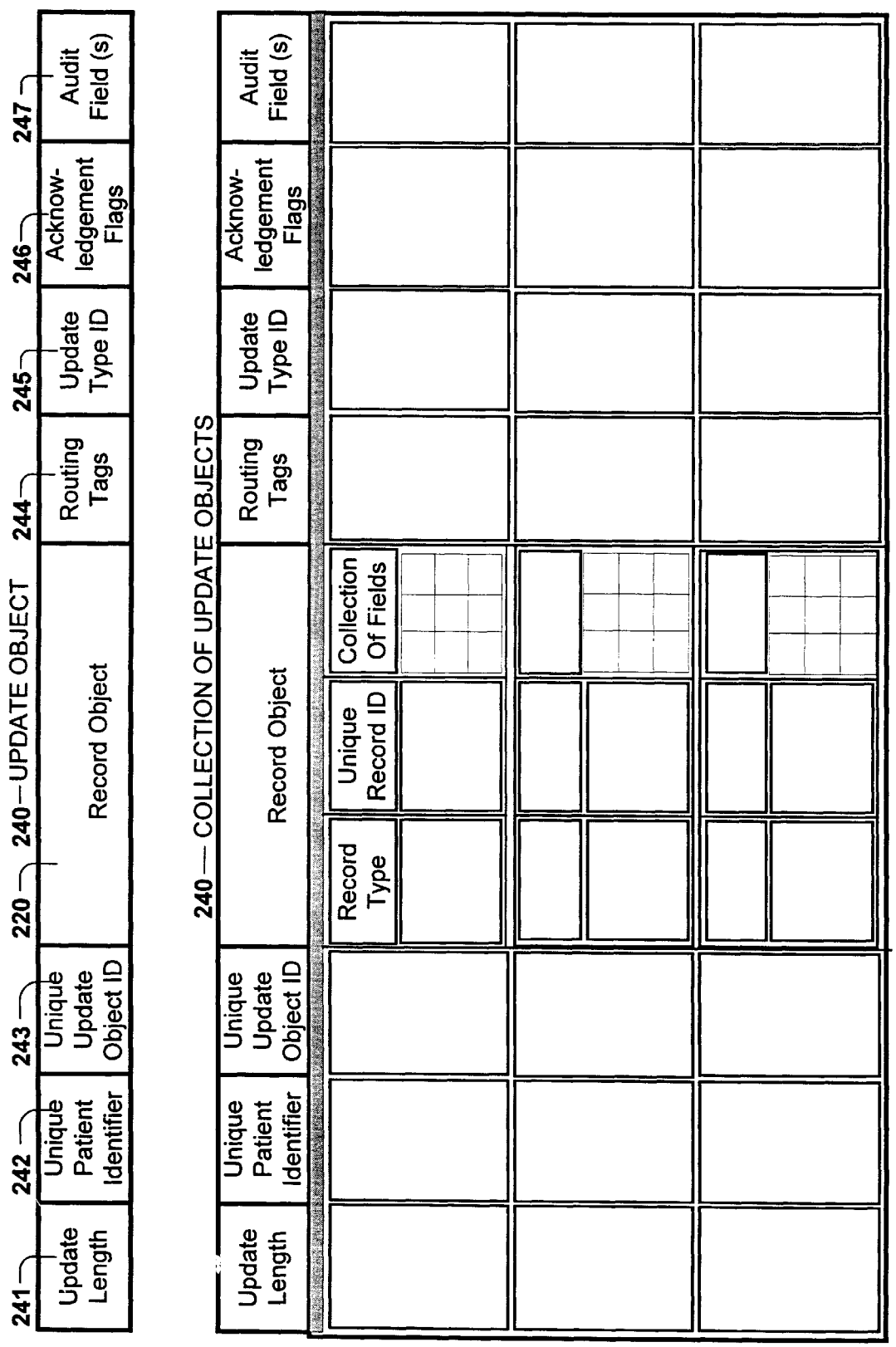
FIG. 4 is a block diagram illustrating the presently preferred update object data structure.

The invention utilizes numerous classes. The fundamental classes of objects used in the system are: field objects 200 (FIG. 2), record objects 220 (FIG. 3) and update objects 240 (FIG. 4).

These objects are generated at all POS stations. They are then distributed to other POS stations and to PDCs, utilizing their own self-contained identification tags and using the rule sets which exist in various parts of the system.

For demonstration and discussion purposes, each of these objects can be depicted in the form of a "table"; although, in the present embodiment, the individual objects and collections of these objects, do not actually exist in traditional "table" form.

Traditional "table" structure, such as that used in relational databases, implies rigid columns and rows with fixed field and record sizes. However, in the present invention, each of the objects is of variable length; and all objects are stored in the databases utilizing just as much space as they need. Space is not wasted.

Furthermore, in the present embodiment, data is not identified by the fixed row and column it is stored in; rather it is stored economically in as little space as possible and it is identified using a pointer system which indicates the position and the length of the stored data package.

B Field Objects 200

See FIG. 2.

Field objects are the smallest objects. In the present embodiment, each field object consists of the field type or data type identifier, the field length and the field value. The data type identifier and the field length both describe properties of the field value.

The data type identifier indicates the category of information that the field value falls under, such as: (1) a CPT code identifier of a laboratory test, (2) a "status" indicator, or (3) a "result" indicator.

The field length indicates the amount of storage space that the field value requires.

The field value is the actual value of the data that is being identified, such as: (1) the actual numbers of the CPT code, (2) the actual status of this test, such as the fact that this is a "final result" or (3) the actual result of the test, such as the hematocrit value is "40."

Field type, field length and field value can all be considered column headings of a field "table." Each row in the "table" describes a certain property of the data that is being identified. The entire "table" can be considered a "collection of fields objects" 210 and that collection indicates the basic information that is known about that particular item of data at that time.

In this embodiment, field objects do not exist on their own, but only exist within record objects.

C Record Objects 220

See FIG. 3.

In the present embodiment, a record object consists of a record type identifier, a unique identifier and a collection of fields.

The record type identifier indicates the category of information that the related collection of fields represents, such as: laboratory test ordered, laboratory test result, X-ray test ordered, X-ray test result, etc.

The unique record identifier used in this preferred embodiment is a time stamp. It is the time in seconds measured from midnight Jan. 1, 1970, GMT.

The collection of field objects has been described above. Again, the field value size is flexible, thus making the entire record object variable in size.

The record type, unique record identifier and collection of field objects can all be considered as column headings of a record "table." Each row in the "table," both generally and uniquely identifies the data that is contained in the collection of field objects column.

A record object adds a level of organization to collections of fields.

A record object is the form in which data persists in the various databases throughout the system.

An entire "table" of records is a "collection of records" 230 and it represents, in an organized fashion, all of the data contained in a patient's static medical file.

In this embodiment, record objects do not exist on their own, but only exist within update objects (described below) or within databases.

D Update Objects 240

See FIG. 4.

An update object adds a level of organization to a record object.

The update object essentially wraps identification and processing information around a single record object and becomes the dynamic form of that record object. The update object contains the processing tags that guide each record object from its point of origin to its intended destination database(s) and also the tags that indicate the type of updating process that is to be accomplished when the record arrives at its destination database(s).

The update object is a key element of this preferred implementation. In conjunction with the processing rules that reside throughout the system, the update object allows distributed databases to be updated independently, without the need of creating or accessing a masterfile. It allows the updating process to be completed automatically without the need of human intervention. It also assures the accurate propagation of update information throughout the system. Each update object persists until it has been notified that the information it contains has successfully reached its intended destination(s).

In this embodiment, the update object consists of: an indication of its own length 241, a unique patient identifier 242, a unique update object identifier 243, at least a single record object 220, identification tags of the intended destination(s) of this update object (routing tags) 244, the update object type identifier (database modification tags) 245, acknowledgment flags 246 and a variable number of audit fields 247.

Each update object contains an indication of its own length 241. This allows for conservation of space throughout the system.

Since the update object is dynamic and moves through the system, it must contain a unique patient identifier 242. The present embodiment utilizes the PDC's unique serial number for this purpose. Other patient identifiers are possible.

This embodiment uses an update time stamp, similar in form to the record object time stamp and an identifier of the source POS station as the unique update object identifiers 243. Other unique identifiers could also be used.

Each update object contains at least a single record object 220 as described previously.

One purpose of the update object is to identify which of the distributed databases in the system this particular record object should be directed to; and this task is accomplished using the identification tags of the intended destination(s) 244. Using these tags and the rule sets that exist in various parts of the system, the update object routes itself to the appropriate independent databases.

Furthermore, when the update object arrives at the destination databases, it interacts with the rule sets contained there and deposits its record object in the databases according to its update type identifier 245.

In the present embodiment, the update type identifier indicates the type of processing action that is intended when the update object reaches its destination database(s), such as: (a) add the enclosed record object to the collection of records, (b) delete a record that is already in the database, or (c) replace a record object that is already in the database with this new record object.

Whereas record objects are intended to be persistent, update objects are transient. They exist for the purpose of directing the processing of the record object they contain. When that purpose has been achieved, the update object, as an entity, can be deleted. The acknowledgment flags 246 are this system's method of determining how long a particular update object needs to persist in any particular location. Essentially, acknowledgment flags are indicators of all of the specific destinations that a particular update object must reach.

In operation, it is a copy of each update object that is actually propagated through the system. Each update object persists at its own originating station; and a copy of that object persists at each subsequent station along its propagating route.

The original object and the copies, all persist, until they receive notification, in the form of feedback acknowledgments, that the appropriate copies have been successfully received at all locations in the system for which the original update object was intended.

As acknowledgments are received from each intended location, the flag 246 for that location is inactivated. When all acknowledgments have been received and all flags inactivated, the update object is deleted from that particular part of the system, because it is no longer needed there.

Therefore, in a static state, a particular patient's medical file will only include a collection of record objects 230. There will not be a collection of update objects 250. This will indicate that all of this patient's medical data has been successfully distributed to all of the independent databases that need it.

For accuracy and security purposes, each update object contains a varied number of fields with auditing tags 247. In the present embodiment, combinations of time stamps and an identifier of the machine that generated the update object are used for audit functions. Other identifiers and audit protocols are possible.

E Databases 260

Figure 5:
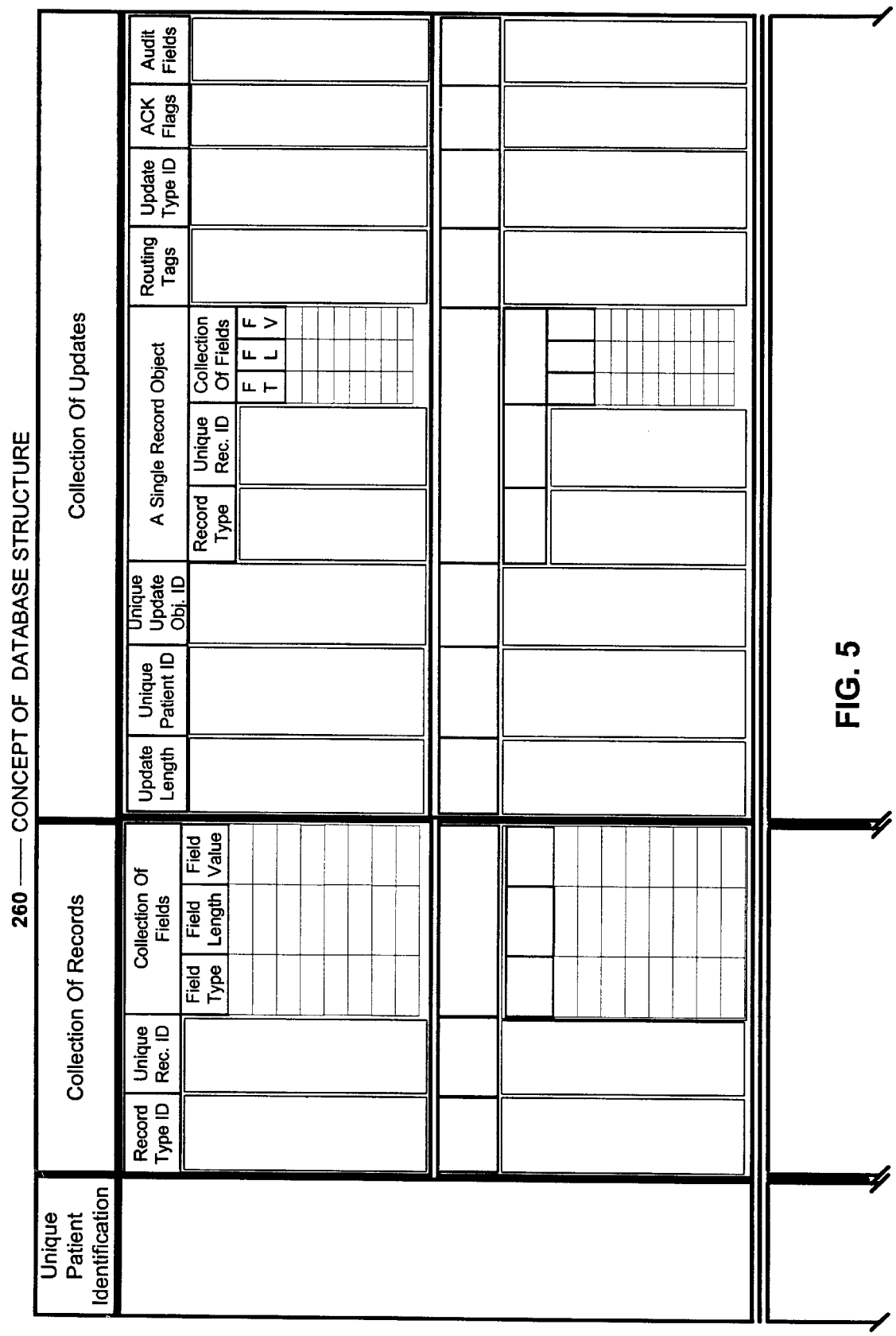
FIG. 5 is a table diagram illustrating the overall database structure employed by the presently preferred implementation.

See FIGS. 5 and 6.

In the present embodiment, object-oriented databases exist in each PDC 103, in each POS station 122, and in the administrative services system 152. In addition, the presently constructed administrative services system contains a relational database 154, using a commercially available database manager.

The object-oriented databases allow rapid storage and retrieval of data in an application specific form. They store data in a format that is efficient and appropriate for patient encounters at medical point-of-service locations.

The flexibility in size of the field, record and update objects allows economical use of space.

In the present embodiment, the distributed databases contain collections of record objects 230 (FIG. 3) and collections of update objects 250 (FIG. 4). These are primarily accessed by a key patient identifier, which presently is a unique patient serial number. The system also allows data access via demographic information, code numbers, data type identifiers and the like.

All of these object-oriented databases are flexible in size and format. They do not have the rigid structure and space restrictions of the traditional database models, such as the table structure of the relational database, with its rigid rows and columns, or records and fields.

Although the field, record and update objects do not actually exist in table form in the preferred embodiment, an "embedded table" format 260 can be used to describe the concepts of the present system.

Referring to FIG. 4, a collection of field objects can be depicted as a "table." The column headings are field type, field length and field value. The rows identify a particular item of data. This "table" exists embedded within a record object.

A collection of record objects can be depicted as another "table," with the column headings of record type, unique record identifier and collection of field objects "table." Each row is a single record object. This collection of records "table" can be embedded in the overall database "table."

A collection of update objects can be depicted as another "table," with the column headings of: update length 241, unique patient identifier 242, unique update object identifier 243, a record object "table" containing its collection of field objects "table" 220, identification tags of intended destinations 244, update type identifiers 245, acknowledgment flags 246 and audit fields 247. Each row is a single update object. This collection of updates "table" can be embedded in the overall database "table," just the same as the collection of records "table."

The database "table" has column headings of unique patient identifier, collection of records "table" and collection of updates "table." Each row contains the entire medical file of a particular patient.

As mentioned previously, in the present embodiment, the administrative services system also contains a relational database and a database conversion system for coupling the object-oriented and the relational databases.

The purpose of the relational database is to include its generally known management and administrative advantages in the present system.

IV Technical Structure

See FIG. 6.

A Portable Data Carrier 100

The presently preferred portable data carrier is a microprocessor and memory-based smart card, that conceptually has four principle subsystems: a communication manager 101, a file manager 102, a file system (database) 103 and a security manager 104.

The invention is designed to use the smart card command set by which commands are input and output through the serial communication port via the communication manager.

Smart card requests include security requests and file requests which are directed to the security manager and file manager respectively. The file manager will not allow memory read/write operations to the internal file system database unless authorized by the security manager. Authorizations are the result of bi-directional communications between the security manager and the file manager.

In the presently preferred embodiment, all patient information data is stored as a collection of record objects in the file system database. Although other structures are possible, the present system utilizes electronically erasable programmable read-only memory (EEPROM), because of its ability to retain information even when external power is turned off.

B Point-of-service Stations 110

In the presently preferred embodiment, the subsystems of the POS stations are: the user interface 111, the database manager 116, the database 122, the patient manager 123, the PDC manager 124, the communication manager 128.

(1) The user interface 111 generates and initiates the propagation of record objects and update objects. It also generates the user display screens that the POS station operator sees.

The user interface contains: a controller module 112, a view module 113 and a data model generation module 114. It accesses the system graphical interface of the operating system 115.

The controller module 112 responds to the PDC presence signals transmitted to it and initiates the user interface's response to the PDC's presence. It is also the principle connection to the presentation manager of the operating system.

The data model generation module 114 constructs the record objects and update objects with the appropriate tags attached, sends the update object to the controller module, which then transmits the update object to the rest of the system.

In the presently preferred embodiment, much of the processing that takes place within the user interface is invisible to the user. The user interface is able to communicate through the controller module with the rest of the system, while concurrently sending displays to the presentation manager for the station operator to view. A separate view module 113 is provided for that purpose.

Information appropriate for presentation to the station operator is selected from the controller module and the data model generation module, assembled into the appropriate display and transmitted to the presentation manager of the operating system 115. The presently preferred embodiment operates in a fully concurrent fashion, so that the controller module and the data generation module can construct data objects, communicate with the PDC and handle data routing and updating functions while the view module concurrently displays information to the station operator.

This offers an important advantage in the present embodiment because communication with the station operator and communication with the PDC are typically the lowest throughput links in the system. The present configuration takes advantage of this arrangement, allowing many data processing tasks to be performed concurrently while the system is reading and writing to the PDC and also while the station operator is interacting with the system through the user screen. During typical operation, the station operator can interact with the user screen, inputting information about the patient, or about the diagnosis or procedures to be performed, without noticing any degradation in system performance as the PDC is concurrently being read and updated.

(2) The POS database manager 116 controls access to the database. It contains: a record object manager 117, an update object manager 118, a data engine 119, an index engine 120 and codes tables subsystem 121.

The index engine coupled to the data engine provides access to the database. As mentioned previously, the access is via serial numbers, demographic information, code numbers, data type and the like.

The data engine 119 controls the storage and retrieval of data from the database storage subsystem. The data engine is coupled to both the record object manager 117 and the update object manager 118. Collectively, these two object managers contain the rule sets by which medical information objects are processed according to the processing tags embedded within the data objects.

The codes table subsystem 121 can contain numerous types of codified information. The present system includes standard medical CPT and ICD-9 code tables, as well as lists of authorized physicians and list of authorized medications.

(3) The POS database 122 is object-oriented. It is flexible in size. It stores and retrieves data according to key identifiers, which include unique patient serial numbers, demographic information, code numbers and data type. Data is stored as collections of record objects 230 (FIG. 3) and as collections of update objects 250 (FIG. 4).

(4) The patient manager 123 is the coordinator of the POS station. It communicates with the user interface 111, the database manager 116, the PDC manager 124 and the communication manager 128. It contains major rule sets relating to data processing, such as routing update objects and modifying databases. These rule sets will be described later.

(5) The PDC manager 124, contains; a PDC presence monitor 125 and a PDC database manager 126.

The PDC presence monitor detects the presence of a PDC when it is installed in the read/write port.

The PDC database manager handles access and security functions. It assures that the PDC conforms to the physical specifications of the system and that the PDC is not fraudulent or defective. It also copies the record objects from the PDC database. It then retrieves any update objects that are stored in the POS database and applies these updates to the PDC collection of records, thus making the PDC records the most current in the system. Copies of this updated collection of records are then sent to both the PDC and the POS databases.

In order to save space and time, the PDC database manager performs the necessary processing steps to determine which fields need to be updated, so that only those fields are written to the PDC.

The PDC database manager is resident within the POS station and has greater throughput capacity than the PDC. While selective updating of the PDC is presently preferred for throughput reasons, the invention can be implemented in alternate ways, such as downloading a complete copy of the updated collection of records.

(6) The communication manager 128 controls the POS station's bidirectional communication with the switching station. In the presently preferred embodiment, this communication takes place using asynchronous modems, although any standard communication system could be used. The communicated data is encrypted for security purposes. The communication manager 128 is able to both initiate and receive calls over a communication channel.

The communication manager interacts with the application layer 129, that is in turn connected to the successive layers of the open system's OSI architecture, namely presentation layer 130, session layer 131, transport layer 132, network layer 133, physical 134 and data link 135 layers. These layers ultimately communicate with the transmission medium.

C Switching Station 140

In the presently preferred embodiment, the switching station provides a conduit for keeping the various independent databases current. It contains rule sets for routing update objects between POS stations, according to the routing tags contained in the update objects. This is an alternate communication channel to the PDC-POS connection and may be utilized when the PDC is not directly available as the data transport medium.

In the present system, the switching station temporarily stores a local copy of each update object that it transmits. The local copy remains in memory at the switching station until all destination POS stations have acknowledged successful receipt of the update object. It is then deleted from the switching station memory.

In this embodiment, the switching station also sends a copy of each update object to the administrative services system. Although this connection provides access to some administrative services, such as data backup, auditing and billing, the integrity of the network does not depend on this connection. The system functions well without needing to access a masterfile.

In the presently preferred embodiment, the switching station contains two subsystems: a communication manager 141 and an update manager 142.

The communication manager 111 is configured to communicate bidirectionally with each POS station. In the present embodiment, this is achieved via asynchronous modems, although other communication channels are possible. For security purposes, the transmitted data is encrypted. The communication manager 141 is able to both initate and receive calls over the communication channel.

The communication manager also handles bidirectional communication with the administrative services system. Local or wide area networks can both be utilized depending on the geographic distribution of the system. In the present embodiment, TCP/IP protocol is used with ISDN and ethernet connections. Other protocols and connections can certainly be used.

The update manager 142 contains the rule sets for routing update objects between POS stations. Although it can be configured otherwise, in the present embodiment, the POS station of the patient's primary physician and the administrative services system both receive a copy of every update object pertaining to that patient. Copies of an update object are also sent to the ordering physician and to other various POS stations as may be designated on the update objects destination tags.

For example, when a consultant physician orders a laboratory test, the patient goes to the laboratory and has the test performed. The laboratory's POS station generates the update object containing the result of the test. That update object is: (1) stored in the laboratory's database and (2) transmitted to the switching station. From the switching station, it goes to: (3) the consultant physician's office, (4) the primary physician's office and (5) the administrative services station. From the primary physician's office or the consultant's office, the result is transmitted to: (6) the patient's PDC.

In this example, when the above process has been completed, the test result will have been successfully and automatically propagated to six independent locations, without needing to access a central database or masterfile, and without requiring the POS stations to be physically connected to each other.

Furthermore, the update object remains "alive" in the system, until assurances, in the form of acknowledgments, have been received, indicating that the record object it contains has successfully reached all of its designated databases.

D Administrative Services System 150

In the presently preferred embodiment, the administrative services system consists of: a communication manager 151, an object-oriented database 152, a database conversion system 153, a commercially available relational database 154 and "customer" services 155.

(1) The communication manager 151 controls communication with the switching station as described above. Direct communication between the administrative services system and the POS stations is possible, but is not presently configured, mainly for security purposes.

(2) The presently preferred object-oriented database 152 is application specific. It is configured according to the "embedded table" architecture described previously. It contains a key patient identifier, collections of record objects and collections of update objects.

It essentially contains a duplication of each of the PDC and POS databases, with the added feature that all update objects persist here indefinitely, primarily for auditing purposes.

Although the presently preferred distributed database architecture is relatively fail-safe on its own because it distributes the data independently throughout the system and does not rely on a central station or masterfile, the administrative services system's database can be used to backup the distributed PDC and POS databases when necessary.

(3) The database conversion system 153 translates the information from the object-oriented structure to a relational database structure. This is accomplished by individually selecting record objects from the object-oriented database and depositing them in fixed field and record relational tables.

(4) In the presently preferred embodiment, a relational database architecture, IBM's DB/2, 154 is included to accommodate interaction with a plurality of external systems and services.

It allows the present invention to interact easily and efficiently via widely used standard protocols and query languages. It facilitates communication with healthcare providers, managers, payers and researchers. It allows the present invention to provide services, such as the "customer" services described below.

(5) "Customer" services 155 are the ancillary management-type services provided by this system to patients, healthcare providers, managers, payers and researchers. These services include, but are not limited to, data backup, billing, payment, account settlement, medical and financial auditing, report generation, quality control and risk management.

V Describing Data Flow via Processing Rules

See FIGS. 7, 8, 9, 10, 11 and 12.

A An Overview of the Processing Rules

In the presently preferred embodiment, each patient's medical file is kept current at numerous independent databases by routing medical data through the system via update objects that interact with strategically placed rule sets.

The update objects are generated at all POS stations and in the administrative services system.

Figure 7:
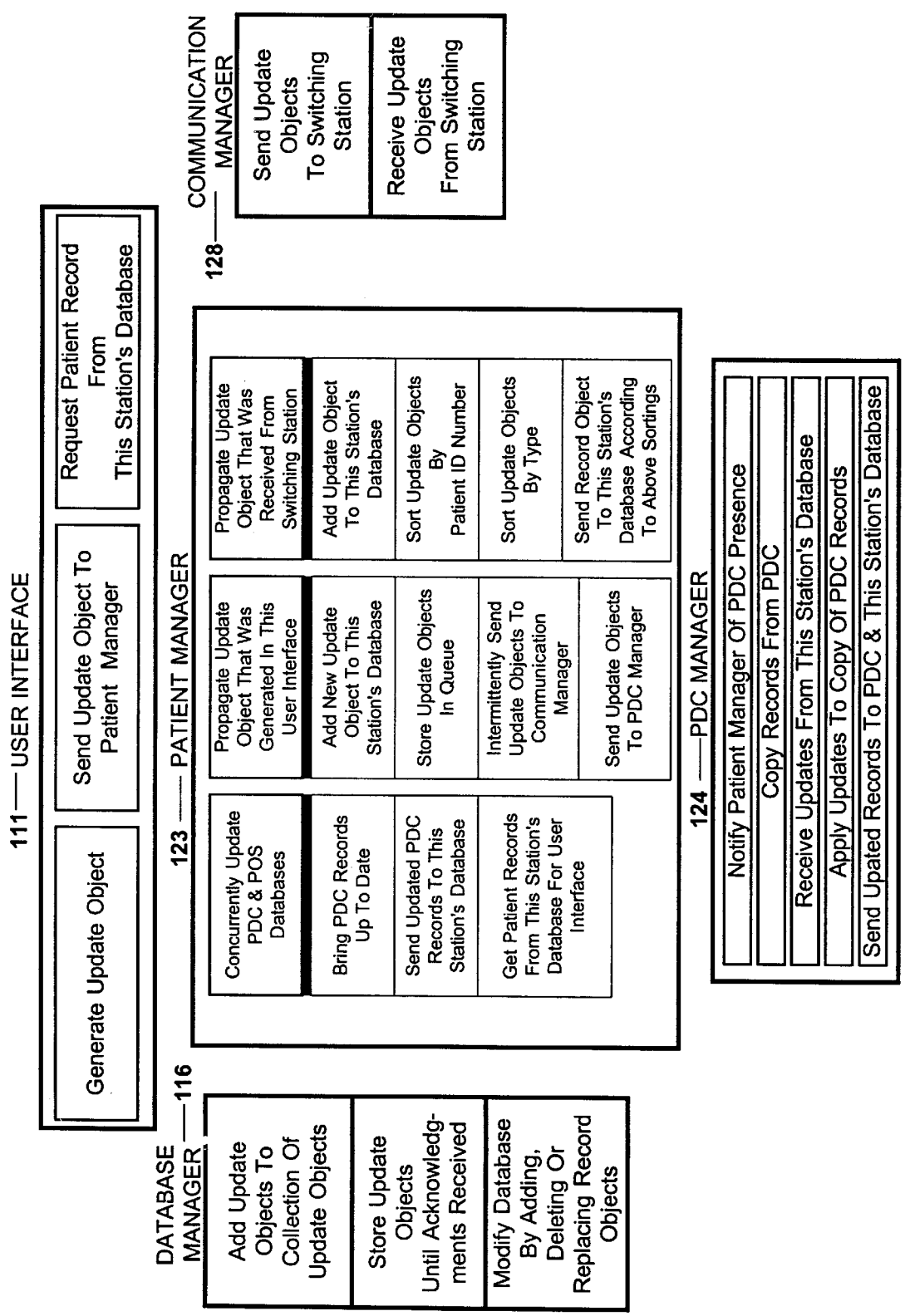
FIG. 7 is a block diagram describing the rules set of the presently preferred implementation, illustrating the presently preferred locations at which the rules are implemented.

The general rules for processing update objects are located within each POS station, in the switching station and in the administrative services system. The general processing rules, as shown in FIGS. 7 and 8, are distributed as follows:

User Interface Ill
Generate update object
Send update object to patient manager
Request patient record from this POS database
Patient Manager 123
Concurrently update PDC and POS databases
Bring PDC records up to date
Send updated PDC records to this POS database
Get patient records from this POS database for user interface
Propagate update object that was generated in this user interface
Add new update object to this station's database
Store update objects in queue
Intermittently send update objects to the communication manager
Send update objects to PDC manager
Propagate update object that was received from the switching station
Add update object to this station's database
Sort update objects by patient ID
Sort update objects by type
Send record objects to this station's database according to the above sorting
Database Manager 116
Add update object to collection of update objects
Store update objects until acknowledgments are received
Modify database by adding, deleting, or replacing record objects
PDC Manager 124
Notify patient manager of PDC presence
Copy records from the PDC
Receive updates from this POS station's database
Apply updates to copy of PDC records
Send updated records to PDC and this station's database
Communication Manager 128
Send update objects to switching station
Receive update objects from switching station
Switching Station 140
Receive update objects from POS stations and administrative services system
Route update objects to designated POS stations
Route update objects to administrative services system
Store update objects until acknowledgments are received
Send update objects to POS stations and administrative services system B Specific Processing Rules Within a POS Station In the present embodiment, within each POS station, each update object 240 (FIG. 4) is generated in the user interface 111. From there, it is routed through the patient manager 123 to the database manager 116, the PDC manager 124 and the communications manager 128. See FIG. 6. This routing is accomplished by following the rules which define the interactions among these various subsystems.

Figure 9:
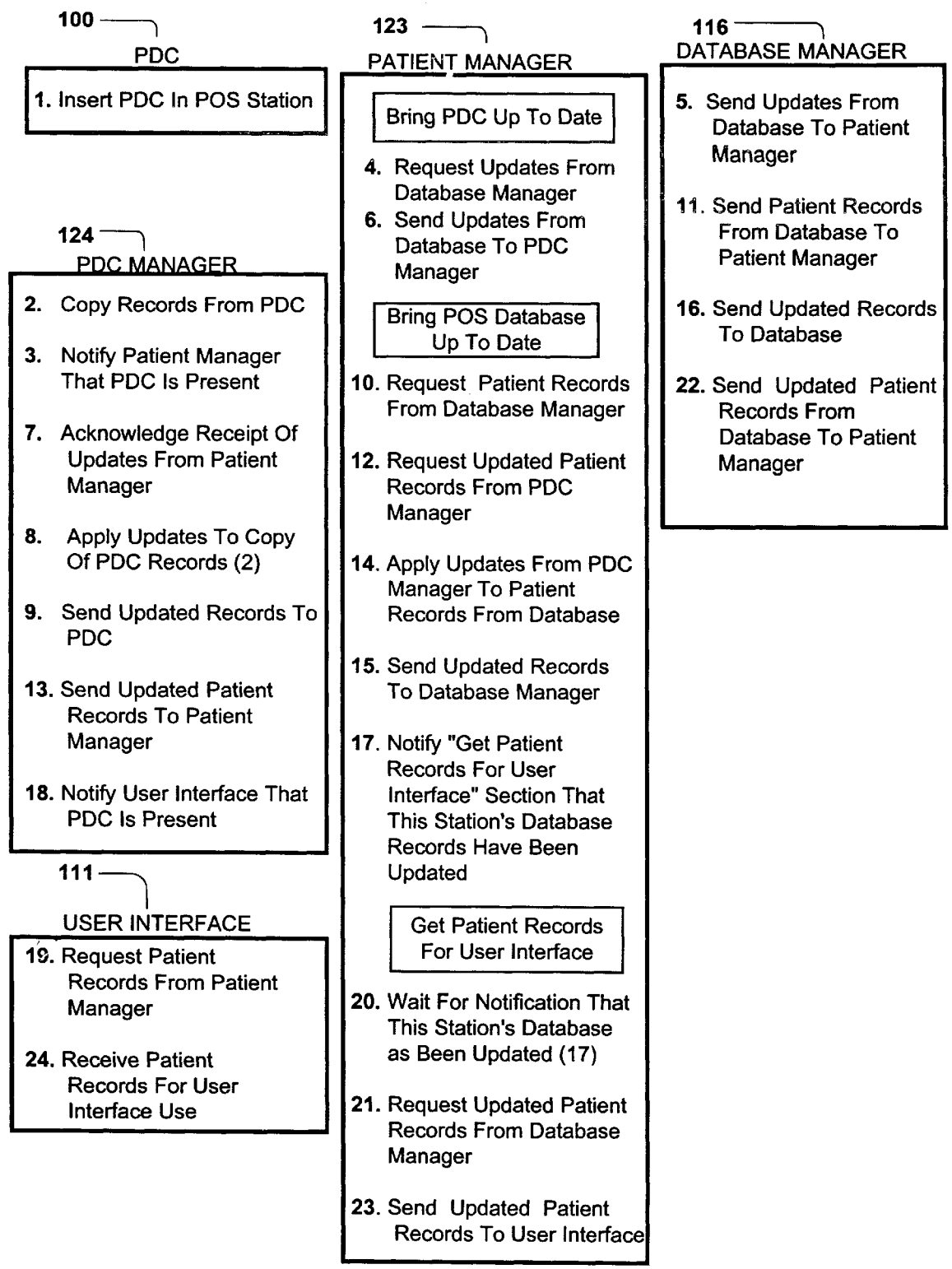
FIG. 9 is a block diagram illustrating the rules set used by the presently preferred embodiment to handle communications and updates between the portable data carrier and point-of-service station databases.
Figure 10:
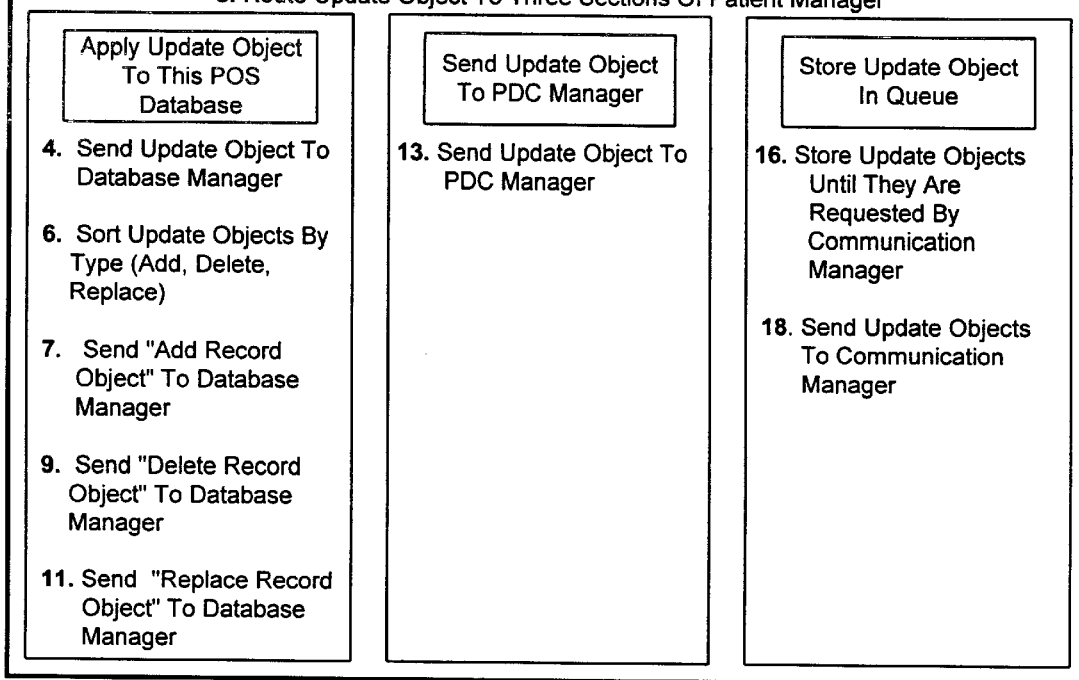
FIG. 10 is a block diagram illustrating the process by which an update object generated by a point-of-service station is propagated.
Figure 12:
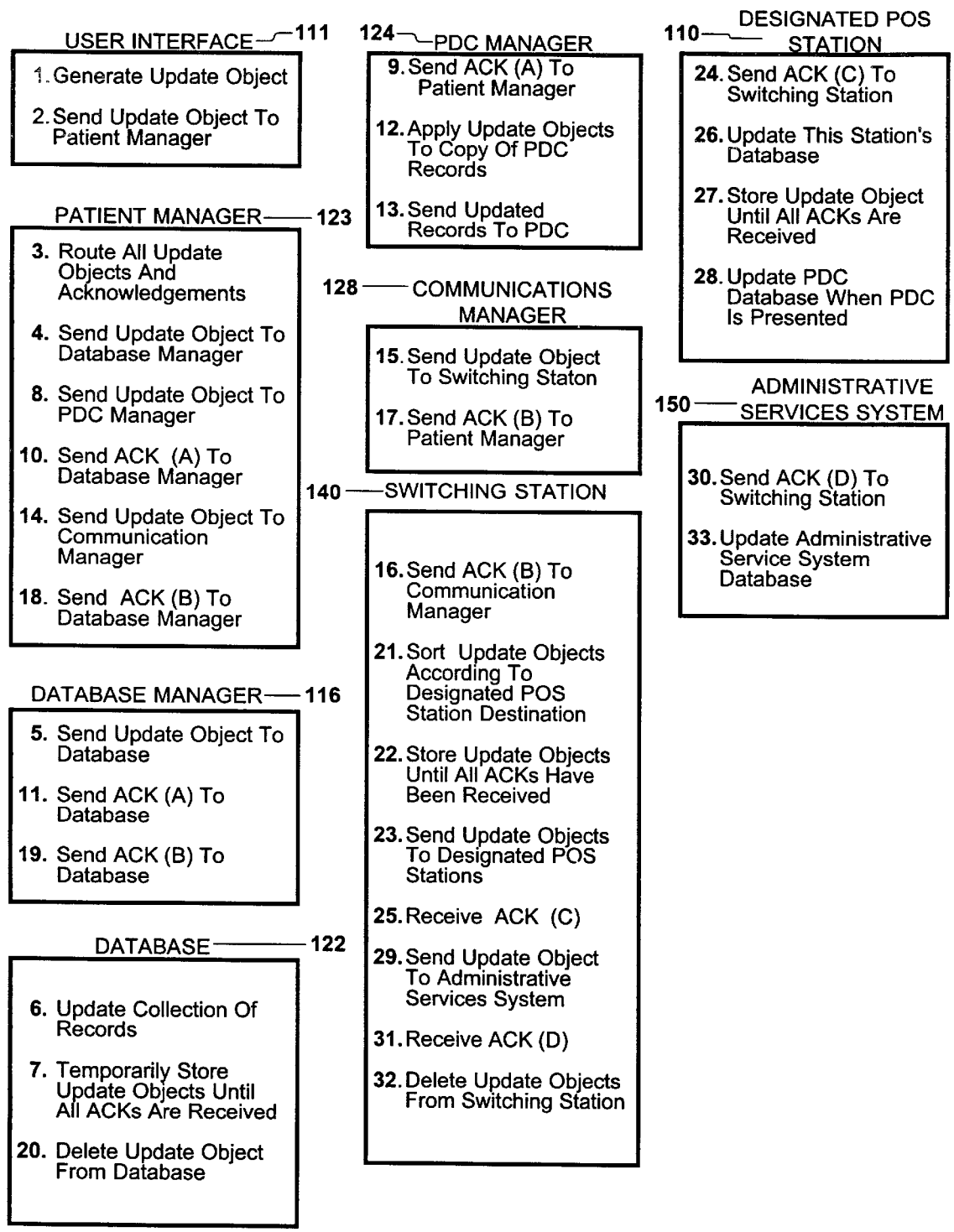
FIG. 12 is a block diagram illustrating the processing rules employed by the preferred embodiment in routing an update object through the entire system.

The rules themselves can be divided into sets based on the several different routing functions that the POS station can accomplish. These functions are: (1) concurrently updating the PDC and POS databases when a PDC is presented for service (FIG. 9), (2) propagating an update object that was generated in this POS station (FIG. 10) and (3) propagating an update object that was received from the switching station (FIG. 11). Each of FIGS. 9–11 show, through a series of sequentially numbered steps, the order in which the rules are implemented.

(1) Concurrently updating the PDC and POS databases when a PDC is presented for service (FIG. 9):

| | |
|---|---|
| 1 | Insert PDC in POS station. |
| 2 | PDC manager copies the records from the PDC. |
| 3 | PDC manager notifies the patient manager that the PDC is present. |
| 4 | Patient manager requests updates from the database manager. |
| 5 | Database manager sends the updates from the database to the patient manager. |
| 6 | Patient manager sends the updates from the database to the PDC manager. |
| 7 | PDC manager acknowledges processing of updates from the patient manager. |
| 8 | PDC manager applies updates to copy of PDC records. |
| 9 | PDC manager sends updated records to PDC. |
| 10 | Patient manager requests patient records from the database manager. |
| 11 | Database manager sends patient records from the database to the patient manager. |
| 12 | Patient manager requests the updated patient records from the PDC manager. |
| 13 | PDC manager sends the updated patient records to the patient manager. |
| 14 | The patient manager applies the updated records from the PDC manager to the patient records from the database. |
| 15 | Patient manager sends the updated records to the database manager. |
| 16 | Database manager sends the updated records to the database. |
| 17 | Patient manager notifies its "get patient records for user interface" section that this station's database records have been updated. |
| 18 | PDC manager notifies the user interface that a PDC is present. |

| | |
|---|---|
| 19 | User interface requests the patient records from the patient manager. |
| 20 | Patient manager waits for notification that this station's database has been updated. |
| 21 | Patient manager requests the updated records from the database manager. |
| 22 | Database manager sends the updated records from the database to the patient manager. |
| 23 | Patient manager sends the updated patient records to the user interface. |
| 24 | User interface receives the patient records for interface use. |

At the end of this series of transactions, both the PDC database 103 and the POS database 122 are identical and current. The two databases have updated each other; and the updated records are ready for use at the user interface 111.

Since this embodiment utilizes a multitasking operating system, the POS station operator can interact with the user interface with no perceived delay, while the PDC and POS databases are interrogating and updating each other.

(2) Propagating an update object that was generated at this POS station (FIG. 10):

| | |
|---|---|
| 1 | The user interface generates a new update object. |
| 2 | The user interface sends the update object to the patient manager. |
| 3 | Patient manager routes the update object to three of its subsections; see steps (4), (13) and (16). |
| 4 | The patient manager sends the update object to the database manager. |
| 5 | The database manager adds the update object to the collection of update objects in the database. |
| 6 | The patient manager sorts the update objects by type (add, delete, replace). |
| 7 | The patient manager sends an "add this record object" message to the database manager. |
| 8 | The database manager adds the record object to the database. |
| 9 | The patient manager sends a "delete this record object" message to the database manager. |
| 10 | The database manager deletes the record object from the database. |
| 11 | The patient manager sends a "replace this record object" to the database manager. |
| 12 | The database manager replaces the record object in the database. |
| 13 | The patient manager sends the update object to the PDC manager. |
| 14 | The PDC manager applies the updates to the PDC manager's copy of the PDC records. |
| 15 | The PDC manager sends the updated records to the PDC. |
| 16 | The patient manager stores the update objects until they are requested by the communication manager. |
| 17 | The communication manager intermittently requests updates from the patient manager. |
| 18 | The patient manager sends update objects to the communication manager. |
| 19 | The communication manager sends update objects to the switching station. |

At the end of this series of transactions, a new update object 240 has been generated, stored in the POS database 122, transferred to the PDC database 103 and sent to the switching station 140. By utilizing a multitasking operating system, all of these transactions can essentially occur simultaneously.

(3) Propagating an update object that was received from the switching station (FIG. 11):

| | |
|---|---|
| 1 | The communication manager of the POS station receives an update object from the switching station. |
| 2 | The communication manager sends the update object to the "apply update objects to this station's database" section of the patient manager. |
| 3 | The patient manager sorts the update objects by patient identification. |
| 4 | The patient manager sends the update objects to the database manager based on patient identification. |
| 5 | The database manager adds the update objects to the collection of updates in this station's database based on patient identification. |
| 6 | The patient manager sorts the update objects by type (add, delete, replace). |
| 7 | The patient manager sends an "add this record object" message to the database manager. |
| 8 | The database manager adds the record object to this station's database. |
| 9 | The patient manager sends a "delete this record object" to the database manager. |
| 10 | The database manager deletes the record object from this station's database. |
| 11 | The patient manager sends a "replace this record object" to the database manager. |
| 12 | The database manager replaces the record object in this station's database. |

At the end of this series of transactions, an update object 240 that has been received from the switching station 140, has been deposited in this POS station's database 122. The database is modified appropriately; and if so designated, the update object persists until it is successfully transmitted to a PDC database 103.

C Processing Rules for Routing an Update Object Through the Entire System (FIG. 12):

In the present embodiment, each update object is generated and propagated within a POS station according to the above rules. The update object is then routed to the switching station for propagation through the rest of the system.

The switching station acknowledges receipt of every update object from each POS station. It then routes all update objects to the administrative services system. For functions such as data backup, system security and auditing, a copy of every update object is retained in an administrative services database indefinitely.

The switching station also routes each update object to the POS stations designated on the update objects destination tags. In the present embodiment, all update objects will at least be routed to the physician who ordered the procedure that generated the update object and to the patient's primary physician.

For example, if a consultant physician orders a laboratory test, the destination tag on the update object that contains the test result will indicate that the update should be sent to that consultant. The rule set in the switching station will read the update object and recognize that the physician who ordered the test is a consultant and not the patient's primary physician; so it will also route the update object to the primary physician.

The switching station stores a copy of each update object until it receives an acknowledgment from each of the destination POS stations that the update object has been successfully received. When all acknowledgments have been received, the update object is deleted from the switching station.

The following are the rules that define the propagation of an update object through the entire system (FIG. 12):

| | |
|---|---|
| 1 | The user interface in the initial POS station generates an update object. |
| 2 | The user interface sends the update object to the patient manager. |
| 3 | The patient manager routes all update objects and acknowledgments. |
| 4 | The patient manager sends the update object to the database manager. |
| 5 | The database manager sends the update object to the database. |
| 6 | The collection of record objects within the database is updated. |
| 7 | The update object is temporarily stored until all acknowledgments are received. |
| 8 | The patient manager sends the update object to the PDC manager. |
| 9 | The PDC manager sends an acknowledgment (A) to the patient manager that it has received the update. |
| 10 | The patient manager sends that acknowledgment (A) to the database manager. |
| 11 | The database manager sends that acknowledgment (A) to the update object in the database. |
| 12 | The PDC manager applies the update object to its copy of the PDC records. |
| 13 | The PDC manager sends the updated records to the PDC. |
| 14 | The patient manager sends the update object to the communication manager. |
| 15 | The communication manager sends the update object to the switching station. |
| 16 | The switching station sends an acknowledgment (B) to the communications manager that it received the update. |
| 17 | The communications manager sends that acknowledgment (B) to the patient manager. |
| 18 | The patient manager sends that acknowledgment (B) to the database manager. |
| 19 | The database manager sends that acknowledgment (B) to the update object in the database. |
| 20 | The update object is deleted from the database since it has received the appropriate acknowledgments (A) and (B). |
| 21 | The switching station sorts the update object according to designated POS station destinations. |
| 22 | The switching station stores update objects until all acknowledgments have been received. |
| 23 | The switching station sends the update object to designated POS stations. |
| 24 | The POS station sends acknowledgment (C) of receipt of the update object to the switching station. |
| 25 | The switching station receives the acknowledgment (C). |
| 26 | The POS station updates its own database just like the initial POS station. |
| 27 | The POS station stores the update object until all acknowledgments have been received. |
| 28 | The POS station updates the PDC database when a PDC is presented. |
| 29 | The switching station sends the update object to the administrative services system. |
| 30 | The administrative services system sends acknowledgment (D) of receipt of the update object to the switching station. |
| 31 | The switching station receives acknowledgment (D) from the administrative services system. |
| 32 | The update object is deleted from the switching station because it has received the appropriate acknowledgments (C) and (D). |
| 33 | The administrative services system updates its own database. |

At the end of this series of events, the patient's PDC database 103, as well as all designated POS databases 122 and the administrative services system database 150 are all synchronized and current. See FIG. 6. All record objects 220 (FIG. 3) have been deposited appropriately and acknowledged. All update objects 240 (FIG. 4) have been deleted from the system. And this has all been accomplished without needing to access a masterfile.

We claim:

1. A computer system for maintaining the currency of data in distributed databases, comprising:

a data communication network;

a plurality of physically separate databases, each of said databases including means for communicating with said data communication network, said databases collectively defining said distributed databases;

a processor having interface for supplying an input instruction to modify the contents of the distributed databases;

said processor being coupled to said data communication network;

said processor being operable to generate an update object in response to said instruction and to place said update object in said data communication network;

said update object having a self-contained processing tag for causing said update object to be intelligently routed along said data communication network to at least one of said plurality of databases and for causing said one of said plurality of databases to automatically modify its contents in accordance with said input instruction;

said update object further having an object-oriented data structure that defines independently created field objects and record objects, said field objects and said field objects each having stored attributes that record information about processes performed on those objects;

said data structure encapsulating data for storing information independent of said distributed databases, said data structure defining a nested, hierarchial relationship such that said field objects are encapsulated within said record objects and wherein said record objects encapsulated within said update object;

said update object thereby being configured to automatically store data and to automatically store in said attributes an historic record of processes performed on said data as said update object is routed anywhere throughout said communication network.

2. The system of claim 1 wherein said data communication network comprises a system employing a portable data carrier having memory for storing and transferring data among said plurality of databases.

3. The system of claim 1 wherein said data communication network comprises a telecommunication network.

4. The system of claim 1 wherein said data communication network comprises in combination:

a system employing a portable data carrier having memory for storing and transferring data among said plurality of databases; and a telecommunication network.

5. The system of claim 1 wherein said data communication network is coupled to a routing processor responsive to said processing tag in intelligently routing said update object along said data communication network.

6. The system of claim 1 wherein said processing tag of said update object comprises a data structure for storing a destination datum for causing said update object to be intelligently routed along said data communication network.

7. The system of claim 1 wherein said data communication network is coupled to a routing processor and wherein said processing tag of said update object comprises a data structure for storing a destination datum that is accessed by said routing processor in causing said update object to be intelligently routed along said data communication network.

8. The system of claim 1 wherein at least one of said databases includes a database processor responsive to said processing tag in modifying the contents of its database.

9. The system of claim 1 wherein said processing tag of said update object comprises a data structure for storing an operation datum based on said input instruction for use in automatically modifying the contents of at least one of said databases.

10. The system of claim 1 wherein at least one of said databases includes a database processor and wherein said processing tag of said update object comprises a data structure for storing an operation datum based on said input instruction that is accessed by said database processor in modifying the contents of said one of said databases.

11. The system of claim 1 wherein said data communication network is coupled to a routing processor having an associated memory for storing a routing rules set.

12. The system of claim 1 wherein said processing tag of said update object comprises a data structure for storing a destination datum that is used according to predefined rules to cause said update object to be intelligently routed along said data communication networks.

13. The system of claim 1 wherein said processing tag of said update object comprises a data structure for storing a destination datum that is used according to predefined rules to cause said update object to be intelligently routed to a selected one of said databases.

14. The system of claim 1 wherein said data communication network is coupled to a routing processor having an associated memory for storing a routing rules set and wherein said processing tag of said update object comprises a data structure for storing a destination datum that is accessed by said routing processor and used in accordance with said routing rules to cause said update object to be intelligently routed along said data communication network.

15. The system of claim 1 wherein said data communication network includes a routing processor having an associated memory for storing a routing rules set and wherein said processing tag of said update object comprises a data structure for storing a destination datum that is used according to said routing rules to cause said update object to be intelligently routed to a selected one of said databases.

16. The system of claim 1 wherein at least one of said databases includes a database processor and an associated memory for storing an operation processing rules set.

17. The system of claim 1 wherein said processing tag of said update object comprises a data structure for storing an operation datum based on said input instruction that is used according to predefined rules to automatically modify the contents of at least one of said databases.

18. The system of claim 1 wherein at least one of said databases includes a database processor and an associated memory for storing an operation processing rules set and wherein said processing tag of said update object comprises a data structure for storing an operation datum based on said input instruction that is accessed by said database processor and used in accordance with said operation processing rules to automatically modify the contents of at least one of said databases.

19. The system of claim 1 wherein said data communication network includes a routing processor having an associated memory for storing a routing rules set and wherein said processing tag of said update object comprises a data structure for storing a destination datum that is accessed by said routing processor and used in accordance with said routing rules to cause said update object to be intelligently routed to at least a selected one of said databases, and wherein at least said selected one of said databases includes a database processor and an associated memory for storing an operation processing rules set and wherein said processing tag of said update object comprises a data structure for storing an operation datum based on said input instruction that is accessed by said database processor and used in accordance with said operation processing rules to automatically modify the contents of said selected one of said databases.

20. A computer-implemented method of maintaining the currency of data in distributed databases consisting of a plurality of physically separate databases, comprising:

receiving an input instruction corresponding to a request to modify data in said distributed databases;

using said input instruction to generate an update object that includes a self-contained processing tag;

said update object further having an object-oriented data structure that defines independently created field objects and record objects, said field objects and said field objects each having stored attributes that record information about processes performed on those objects;

said data structure encapsulating data for storing information independent of said distributed databases, said data structure defining a nested, hierarchial relationship such that said field objects are encapsulated within said record objects and wherein said record objects encapsulated within said update object;

said update object thereby being configured to automatically store data and to automatically store in said attributes an historic record of processes performed on said data as said update object is routed anywhere throughout said communication network;

conveying said update object to at least a selected one of said plurality of databases using said processing tag to cause said update object to be intelligently routed to said selected one of said databases;

further using said processing tag to cause said selected one of said databases to automatically modify its respective contents in accordance with said input instruction.

21. The method of claim 20 further comprising employing a portable data carrier to convey said update object by storing the contents of said update object in said portable data carrier and physically transporting said portable data carrier between said selected databases.

22. The method of claim 20 further comprising using a telecommunication network to transmit said update object between said selected databases.

23. The method of claim 20 further comprising using a data communication network that employs, in combination, a portable data carrier and a telecommunication network and wherein said conveying step is performed by at least one of the following methods:

(a) by storing said update object in said portable data carrier and physically transporting said portable data carrier between said databases and (b) by transmitting said update object over said telecommunication network.

24. The method of claim 20 wherein at least a first one of said plurality of databases has an associated processor and wherein said method further comprises using said associated processor to write to a processing tag a datum indicative of a destination database to which the update object is intelligently routed.

25. The method of claim 20 wherein at least a first one of said plurality of databases has an associated processor and wherein said method further comprises using said associated processor to write to a processing tag a datum to specify a selected one of a plurality of data manipulation processes.

26. The method of claim 20 wherein at least a first one of said plurality of databases has an associated processor and wherein said method further comprises using said associated processor to read said processing tag and to intelligently route said update object to a second one of said plurality of databases in accordance with said processing tag.

27. The method of claim 20 wherein at least a first one of said plurality of databases has an associated processor and wherein said method further comprises using said associated processor to read said processing tag and to route said update object to a communication network.

28. The method of claim 20 wherein at least a first one of said plurality of databases has an associated processor and wherein said method further comprises using said associated processor to read said processing tag and to route said update object to a routing processor coupled to a communication network.

29. The method of claim 20 wherein at least a first one of said plurality of databases has an associated processor and wherein said method further comprises using said associated processor to read said processing tag and to modify the contents of said first database in accordance with said processing tag.

30. The method of claim 20 further comprising conveying said update object over a data communication network to a routing processor.

31. The method of claim 20 further comprising:
conveying said update object over a data communication network to a routing processor; and
using said routing processor to route said update object to at least a second one of said plurality of databases over said data communication network.

32. The method of claim 20 wherein at least a first one of said databases includes an associated processor and wherein said method further comprises storing a routing rules set in a memory addressed by said associated processor and using associated processor to access said routing rules set and said processing tag to cause said update object to be routed along said data communication network.

33. The method of claim 20 wherein said data communication network includes an associated processor and wherein said method further comprises storing a routing rules set in a memory addressed by said associated processor and using said associated processor to access said routing rules set and said processing tag to cause said update object to be intelligently routed to a destination database.

34. The method of claim 20 wherein at least a first one of said plurality of databases has an associated processor and wherein said method further comprises storing an operation processing rules set in a memory addressed by said associated processor and using said associated processor to access said rules set and said processing tag and to modify the contents of said first database.

35. An information system for maintaining the currency of computerized records, comprising:
a first processor with associated first memory for storing a first database of computerized records;
a second processor with second memory for storing a second database of computerized records;
said first and second memories being disposed at physically separate locations;
a smart card having an embedded third processor and associated third memory for storing a third database of computerized records;

said first and second processors each having a port for interfacing with said smart card;
said smart card being:
operable as a client and server to said first and second databases;
physically transportable between said first and second databases; and
operable to propagate information between said first and second databases such that the currency of computerized records is maintained in said first, second and third databases;
wherein said first processor generates an update object for routing an element of information to said second database;
said update object further having an object-oriented data structure that defines independently created field objects and record objects, said field objects and said field objects each having stored attributes that record information about processes performed on those objects;
said data structure encapsulating data for storing information independent of said distributed databases, said data structure defining a nested, hierarchial relationship such that said field objects are encapsulated within said record objects and wherein said record objects encapsulated within said update object;
said update object thereby being configured to automatically store data and to automatically store in said attributes an historic record of processes performed on said data as said update object is routed anywhere throughout said communication network.

36. The information system of claim 35 wherein at least one of said first and third processors operate on both first and third databases to mutually update both first and third databases.

37. The information system of claim 35 wherein at least one of said second and third processors operate on both second and third databases to mutually update both second and third databases.

38. The information system of claim 35 wherein at least one of said processors generates an update object carried by said smart card.

39. The information system of claim 35 wherein said first processor generates an update object for routing an element of information to said second database, said update object including a processing tag to identify at least a selected one of a plurality of data processing operations; and
wherein said second processor operates on the computerized records stored in said second database using said element of information in accordance with said processing tag.

40. A self-updating computer-implemented database system for storing elements of information comprising:
a computer-implemented system for generating an update object that stores an element of information and that includes a processing tag for specifying at least one of a plurality of predefined data manipulation processes and for causing said update object to be intelligently routed to at least one destination;
a second database with associated second processor for receiving said update object;
a second database with associated second processor for receiving said update object;
said update object further having an object-oriented data structure that defines independently created field objects and record objects, said field objects and said field objects each having stored attributes that record information about processes performed on those objects;

said data structure encapsulating data for storing information independent of said distributed databases, said data structure defining a nested, hierarchial relationship such that said field objects are encapsulated within said record objects and wherein said record objects encapsulated within said update object;

said update object thereby being configured to automatically store data and to automatically store in said attributes an historic record of processes performed on said data as said update object is routed anywhere throughout said communication network, said first processor being responsive to the processing tag of said update object to:
(a) modify the contents of said first database in accordance with the data manipulation process specified by said processing tag;
(b) store said update object in said first database; and
(c) convey said update object to said second database in accordance with the destination specified by said processing tag;

said second processor being operative to:
(i) modify the contents of said second database in accordance with the data manipulation process specified by said processing tag; and
(ii) send an acknowledgment of receipt of said update object to said first processor;

said first processor being operative to initiate deletion of said update object from said first database in response to receipt of said acknowledgment from said second processor.

41. The system of claim 40 wherein said computer-implemented system generates said update object in response to input from a user of said database system.

42. The system of claim 40 wherein said second processor is further operative to store said update object in said second database.

43. The system of claim 40 wherein the system includes a third database with associated third processor and wherein said second processor is further operative to convey said update object to said third processor.

44. The system of claim 40 further comprising a data communication network and wherein said first processor conveys said update object to said second processor over said communication network.

45. The system of claim 44 wherein said data communication network comprises a system employing a portable data carrier having memory for storing said update object.

46. The system of claim 44 wherein said data communication network comprises a telecommunication network.

47. The system of claim 44 wherein said data communication network comprises in combination:
a system employing a portable data carrier having memory for storing said update object; and a telecommunication network.

48. The system of claim 44 wherein said data communication network is coupled to a routing processor for reading said processing tag and conveying said update object to at least said second database.

49. The system of claim 40 wherein said first and second databases are disposed at physically separate locations.

50. The system of claim 40 wherein said update object includes means for storing an identification datum that functions as a database key.

51. An information system for maintaining the currency of computerized records, comprising:
a first processor with associated first database of computerized records;
a second processor with associated second database of computerized records;
said first and second databases being disposed at physically separate locations;
a portable data carrier having a third processor and associated third database of computerized records;
said first and second processors each having a port for interfacing with said portable data carrier;
said portable data carrier being operable as a client and server to said first and second databases and physically transportable being said first and second processors to define a first communication channel that is operable to propagate information between said first and second databases;
at least one of said first and second processors having a routing rules set forth for causing at least one of said first and second processors to propagate information between said first and second databases over a second communication channel;
whereby said first and second communication channels collectively operate such that currency of computerized records is maintained in said first, second and third databases;
wherein said first processor generates an update object that is propagated over at least one of said first and second communication channels;
said update object further having an object-oriented data structure that defines independently created field objects and record objects, said field objects and said field objects each having stored attributes that record information about processes performed on those objects;
said data structure encapsulating data for storing information independent of said distributed databases, said data structure defining a nested, hierarchial relationship such that said field objects are encapsulated within said record objects and wherein said record objects encapsulated within said update object;
said update object thereby being configured to automatically store data and to automatically store in said attributes an historic record of processes performed on said data as said update object is routed anywhere throughout said communication network.

52. The information system of claim 51 wherein said portable data carrier is a smart card that includes said third processor and said third database.

53. The information system of claim 51 wherein the first database stores an update object containing a database modification processing tag;
wherein at least one of the first and third processors causes at least one of the first and third databases to be initially modified according to the processing tag and then at least one of the first and third processors updates the other of said first and third databases based on the information in said initially modified database;
and wherein at least one of the second and third processors updates the second database based on the information contained in third database upon the portable data carrier being physically transported to said second database.

54. The information system of claim 51 wherein the first processor generates an update object containing a routing tag and database modification tag, the first processor stores the update object in the first database and sends the update object along said second communication channel to the second processor based on said routing tag and said second processor modifies the second database based on said database modification tag.

55. The information system of claim 51 wherein said first processor has a processing rules set accessed by said first processor to generate an update object for routing an element of information to said second database.

56. The information system of claim 51 wherein said first processor has a first processing rules set accessed by said first processor to generate an update object for routing an element of information to said second database, said update object including a processing tag to identify at least a selected one of a plurality of data processing operations; and
wherein said second processor has a second processing rules set accessed by said second processor to cause said second processor to operate on the computerized records stored in said second database using said element of information in accordance with said processing tag.

57. The information system of claim 51 wherein said second database includes an administrative services system.

58. An information system for maintaining the currency of computerized records in distributed databases, comprising:
a first database with associated first processor;
a second database with associated second processor;
said first and second databases being disposed at physically separate locations;
a first communication channel comprising a portable data carrier having a third database with associated third processor, the portable data carrier being operable as a client and server to said first and second databases and physically transportable between said first and second processors to propagate information between said first and second databases;
a second communication channel accessible by said first and second processors;
a first system for collectively updating said first, second and third databases, wherein:
(a) at least one of said first and third processors is operable to mutually update said first and third databases; and
(b) at least one of said second and third processors is operable to mutually update said second and third databases;
a second system for collectively updating said first and second databases, wherein:
(a) said first processor generates an update object having a processing tag for specifying at least one of a plurality of predefined data manipulation processes and for specifying at least one destination;
said update object further having an object-oriented data structure that defines independently created field objects and record objects, said field objects and said field objects each having stored attributes that record information about processes performed on those objects;
said data structure encapsulating data for storing information independent of said distributed databases, said data structure defining a nested, hierarchial relationship such that said field objects are encapsulated within said record objects and wherein said record objects encapsulated within said update object;

said update object thereby being configured to automatically store data and to automatically store in said attributes an historic record of processes performed on said data as said update object is routed anywhere throughout said communication network,
(b) said first processor modifies the contents of said first database in accordance with the data manipulation process specified by said processing tag;
(c) said first processor propagates said update object to said second processor along said second communication channel in accordance with the destination specified by said processing tag;
(d) said second processor modifies the contents of said second database in accordance with the data manipulation process specified by said processing tag;
whereby the currency of computerized records in said first, second and third databases are maintained current.

59. The system of claim 58 wherein said portable data carrier is a smart card that includes said third processor and said third database.

60. The information system of claim 58 wherein said first processor includes a user interface and wherein said first processor generates said update object based on information supplied through said user interface.

61. The information system of claim 58 wherein the first database stores an update object containing a database modification processing tag;
wherein at least one of the first and third processors causes at least one of said first and third databases to be initially modified according to the database modification processing tag and then at least one of the first and third processors updates the first database based on the information in the initially modified database;
and wherein at least one of the second and third processors updates the second database based on the information in the third database, upon the portable data carrier being physically transported to said second database.

62. The information system of claim 58 wherein the first processor generates an update object containing a routing tag and database modification tag, the first processor stores the update object in the first database and sends the update object along at least one of said first and second communication channels to the second processor based on said routing tag and said second processor modifies the second database based on said database modification tag.

63. The information system of claim 58 wherein said second database includes an administrative services system.

64. A self-updating, computer-implemented distributed database system for storing elements of information comprising:
a computer system for generating and storing data objects that include:
(a) a record object for storing an element of information;
(b) an update object for defining a relationship with at least one associated record object, said update object storing a processing tag;
said update object further having an object-oriented data structure that defines independently created field objects and record objects, said field objects and said field objects each having stored attributes that record information about processes performed on those objects;
said data structure encapsulating data for storing information independent of said distributed databases, said data structure defining a nested, hierarchial relationship such that said field objects are encapsulated within said record objects and wherein said record objects encapsulated within said update objects;

said update object thereby being configured to automatically store data and to automatically store in said attributes an historic record of processes performed on said data as said update object is routed anywhere throughout said communication network, said computer system further generating a database system that comprises a collection of record objects that define a persistent portion of the database and a collection of update objects that define a transient portion of the database;

the database system being responsive to said processing tag for automatically updating the persistent portion of said database;

the database system further including a feedback mechanism comprising a second update object for systematically purging said update objects from the transient portion of the database.

65. The database system of claim 64 wherein said record object includes a field object for storing said element of information.

66. The database system of claim 64 wherein said update object includes an acknowledgement tag accessed by said feedback mechanism in purging said update objects from the transient portion of the database.

67. The database system of claim 64 wherein said processing tag comprises a routing tag and a database modification tag.

68. The database system of claim 64 wherein said record object includes a record identification tag.

69. The database system of claim 64 wherein at least one of said record objects and said update objects employs a variable length data storage mechanism.

70. The database system of claim 69 wherein said variable length storage mechanism uses a pointer system for data storage and retrieval.

71. The database system of claim 64 wherein said database system includes a first database having a first processor and wherein said feedback mechanism uses said first processor to read the processing tag of said update object and to store said update object in the transient portion of the first database.

72. The database system of claim 64 wherein said database system includes a first database having a first processor and a second database having a second processor and wherein said feedback mechanism uses said first processor to read the processing tag of said update object and to route said update object to said second database in accordance with said processing tag.

73. The database system of claim 64 wherein said database system includes a first database having a first processor and a second database having a second processor and wherein said feedback mechanism uses said second processor to generate a second update object having a second processing tag.

74. The database system of claim 73 wherein said second processing tag is an acknowledgement tag.

75. The database system of claim 64 wherein said database system includes a first database having a first processor and a second database having a second processor and wherein said feedback mechanism uses said second processor to transmit a second update object having second processing tag to said first processor.

76. The database system of claim 64 wherein said database system includes a first database having a first processor and a second database having a second processor;

wherein said feedback mechanism uses said first processor to read the processing tag of a first update object and to store said first update object in the transient portion of the first database;

wherein said feedback mechanism uses said first processor to transmit said first update object to said second processor;

wherein said feedback mechanism uses said second processor to transmit a second update object having a second processing tag to said first processor in response to said first update object; and wherein said feedback mechanism uses said first processor to read said second processing tag and to modify said first database by deleting said first update object from said first database in response to said second processing tag.

* * * * *